US011373854B2

(12) United States Patent
Yagyu et al.

(10) Patent No.: US 11,373,854 B2
(45) Date of Patent: Jun. 28, 2022

(54) DEVICE FOR EMITTING ULTRAVIOLET LIGHT

(71) Applicant: Ushio Denki Kabushiki Kaisha, Tokyo (JP)

(72) Inventors: Hideaki Yagyu, Tokyo (JP); Atsushi Imamura, Tokyo (JP); Manabu Mori, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/396,944

(22) Filed: Aug. 9, 2021

(65) Prior Publication Data

US 2022/0068627 A1 Mar. 3, 2022

(30) Foreign Application Priority Data

Sep. 1, 2020 (JP) .............................. JP2020-146836

(51) Int. Cl.
*H01J 61/52* (2006.01)
*H01J 61/54* (2006.01)
(Continued)

(52) U.S. Cl.
CPC .............. *H01J 61/547* (2013.01); *A61L 2/10* (2013.01); *H01J 61/40* (2013.01); *H01J 61/52* (2013.01); *H01J 65/00* (2013.01); *A61L 2202/11* (2013.01)

(58) Field of Classification Search
CPC .......... H01J 61/547; H01J 61/40; H01J 61/52; H01J 65/00; A61L 2/10; A61L 2202/11
See application file for complete search history.

(56) References Cited

U.S. PATENT DOCUMENTS 10,910,210 B2 2/2021 Yagyu et al.
2012/0006995 A1 1/2012 Greuel
(Continued)

FOREIGN PATENT DOCUMENTS

EP 1310298 A1 5/2003
JP H09-302326 A 11/1997
(Continued)

OTHER PUBLICATIONS

An Office Action; "Notice of Reasons for Rejection", mailed by the Japanese Patent Office dated Jun. 22, 2021, which corresponds to Japanese Patent Application No. 2020-146836 and is related to U.S. Appl. No. 17/396,944; with English language translation.
The European search report (under R. 61 or R. 63 EPC) or the supplementary european search report (Art. 153(7) EPC) issued by the European Patent Office dated Jan. 24, 2022, which corresponds to European Patent Application No. 21190073.3-1212 and is related to U.S. Appl. No. 17/396,944.
(Continued)

*Primary Examiner* — Donald L Raleigh
(74) *Attorney, Agent, or Firm* — Studebaker & Brackett PC (57) ABSTRACT

A device for emitting ultraviolet light includes at least one excimer lamp and a housing for the excimer lamp(s). Each excimer lamp has a discharge vessel filled with light-emitting gases, and a pair of first and second electrodes that are placed in contact with the discharge vessel and produce a dielectric barrier discharge inside the discharge vessel. The housing is made of an insulating and heat-resistant resin material. The housing is configured to house the excimer lamp(s), and has a light-emitting window that allows light with a center wavelength in a range from 200 nm to 230 nm emitted from the excimer lamp(s) to exit from the housing.

12 Claims, 3 Drawing Sheets

(51) Int. Cl.
  *H01J 65/00* (2006.01)
  *H01J 61/40* (2006.01)
  *A61L 2/10* (2006.01)

(56) References Cited

U.S. PATENT DOCUMENTS

| | | |
|---|---|---|
| 2015/0073396 A1 | 3/2015 | Randers-Pehrson et al. |
| 2016/0107000 A1 | 4/2016 | Randers-Pehrson et al. |
| 2018/0169279 A1 | 6/2018 | Randers-Pehrson et al. |
| 2019/0160305 A1 | 5/2019 | Randers-Pehrson et al. |
| 2019/0381336 A1 | 12/2019 | Randers-Pehrson et al. |
| 2019/0388706 A1 | 12/2019 | Randers-Pehrson et al. |
| 2020/0085984 A1 | 3/2020 | Randers-Pehrson et al. |
| 2020/0215215 A1 | 7/2020 | Randers-Pehrson et al. |
| 2020/0234941 A1* | 7/2020 | Yagyu .................. A61L 2/10 |
| 2020/0306397 A1 | 10/2020 | Randers-Pehrson et al. |
| 2020/0353112 A1 | 11/2020 | Randers-Pehrson et al. |
| 2021/0187319 A1 | 6/2021 | Randers-Pehrson et al. |

FOREIGN PATENT DOCUMENTS

| | | | |
|---|---|---|---|
| JP | 2007-123069 A | 5/2007 | |
| JP | 2016-036772 A | 3/2016 | |
| JP | 6025756 B2 | 11/2016 | |
| JP | 2018-113116 A | 7/2018 | |
| JP | WO-2018131582 A1 * | 7/2018 | ........... A61L 2/0047 |
| JP | 6558376 B2 | 8/2019 | |
| JP | 2020-099524 A | 7/2020 | |
| WO | 2012/122210 A1 | 9/2012 | |

OTHER PUBLICATIONS

Communication pursuant to Article 94(3) EPC issued by the European Patent Office dated Feb. 4, 2022, which corresponds to European Patent Application No. 21190073.3-1212 and is related to U.S. Appl. No. 17/396,944.

* cited by examiner

DEVICE FOR EMITTING ULTRAVIOLET LIGHT

TECHNICAL FIELD

The present invention relates to a device for emitting ultraviolet light (i.e., UV irradiation device) equipped with one or more excimer lamps.

DESCRIPTION OF THE RELATED ART

In the past, in order to prevent the spread of infectious diseases caused by harmful microorganisms (bacteria, mold, etc.) and viruses, a device for emitting ultraviolet light is disposed to irradiate microorganisms and viruses floating in the space with the ultraviolet light, and inactivate the microorganisms and viruses. Such device may also irradiate microorganisms and viruses attached to various places, such as floors, walls, and surfaces of objects, with the ultraviolet light and inactivate the microorganisms and viruses.

For example, Japanese Patent No. 6,558,376 discloses a UV irradiation device used for sterilization and deodorization treatment of skin and the like. An excimer lamp mounted in the UV irradiation device includes a light-emitting tube having a cylindrical outer tube and a cylindrical inner tube that is coaxial with the outer tube. An annular discharge space is formed between the outer tube and the inner tube. The UV irradiation device also includes an intake and exhaust fan for cooling the excimer lamp, an outer electrode disposed on the outer surface of the light-emitting tube, and an inner electrode disposed on the inner surface the light-emitting tube. A power supply unit applies high-frequency high voltage between the outer electrode and the inner electrode.

Another UV irradiation device is disclosed in Japanese Patent No. 6,025,756. This UV irradiation device emits ultraviolet light with a wavelength of around 200 nm (e.g., excimer light with a wavelength of 207 nm or 222 nm) to sterilize bacteria without damaging human cells. The ultraviolet light with the wavelength of around 200 nm is safe for humans, and can also be used to sterilize spaces and surfaces.

SUMMARY OF THE INVENTION

The discovery of ultraviolet light that can inactivate harmful microorganisms and viruses without harming human cells has led to the expectation that such ultraviolet light can be used to inactivate microorganisms and viruses in a wide range of settings, including facilities where people and animals come and go (hospitals, sports facilities, theaters, restaurants, meeting rooms, restrooms, etc.) and vehicles (airplanes, trains, buses, cars). However, the UV irradiation device described in Japanese Patent No. 6558376 tends to have a large housing structure and is not versatile very much.

The excimer lamp can adjust the wavelength characteristics (wavelength range) of the emitted light depending on the types of discharge gases. If appropriate gases are employed as the discharge gases, it is possible to obtain ultraviolet light that has a center wavelength around 200 nm. Specifically, if krypton bromide (KrBr) gas is used, the excimer lamp can emit light with a center wavelength of 207 nm, and if krypton chloride (KrCl) gas is used, the excimer lamp can emit light with a center wavelength of 222 nm.

However, if the light emitted from the excimer lamp contains the ultraviolet light with a wavelength of less than 190 nm, ozone ($O_3$) can be generated. This is because when ultraviolet light with a wavelength of less than 190 nm is directed into an atmosphere containing oxygen, oxygen molecules are photolyzed to produce oxygen atoms, and ozone is produced by the bonding reaction between oxygen molecules and oxygen atoms. Therefore, when an excimer lamp is turned on in the atmosphere (outside air) and emits a small amount of ultraviolet light with a wavelength of less than 190 nm, a trace amount of ozone may be generated in the atmosphere. This ozone may degrade organic materials such as resin and rubber. Also, if a high voltage is applied between two electrodes of the excimer lamp, atmospheric discharge may take place between the electrodes or atmospheric discharge may take place in a small gap between the electrode(s) and the discharge lamp. The atmospheric discharge may generate a trace amount of ozone that may degrade the organic materials.

One object of the present invention is to provide an ultraviolet irradiation device equipped with one or more excimer lamps that emit light with a center wavelength in the range from 200 nm to 230 nm, and with a more versatile device structure.

According to one aspect of the present invention, there is provided a device for emitting ultraviolet light (ultraviolet irradiation device) that includes at least one excimer lamp and a housing for the excimer lamp(s). Each excimer lamp has a discharge vessel filled with light-emitting gases, and a pair of first and second electrodes that are placed in contact with the discharge vessel and produce a dielectric barrier discharge inside the discharge vessel. The housing is made of an insulating and heat-resistant resin material. The excimer lamp(s) are arranged and enclosed in the housing. The housing has a light-emitting window (light exit window) that allows light emitted from the excimer lamp(s) with a center wavelength in a range from 200 nm to 230 nm to proceed out of the housing.

Because the excimer lamps are enclosed in the housing made from the heat-resistant resin, the inside of the housing is kept warm. This provides the effect of mitigating the UV distortion of the glass that is a material of the discharge vessel. When a small amount of oxygen is present around the excimer lamp(s), the oxygen may be exposed to the ultraviolet rays emitted from the excimer lamp(s) and ozone may be generated, but the thermal decomposition of ozone takes place by the heat retained in the housing. Since the housing is designed to retain the heat therein, there is no need to place a mechanism to cool the excimer lamp(s), for example, inside the housing. This prevents the housing structure from becoming too large, and allows for a highly versatile device structure.

The ultraviolet irradiation device may further include a first electrical conductor electrically connected to the first electrode and extending through the housing, and a second electrical conductor electrically connected to the second electrode and extending through the housing. The first and second electrical conductors may be electrically connected to a power supply unit that supplies power to the excimer lamp(s), and the power supply unit may be disposed outside the housing.

If the power supply unit is disposed outside the housing, components of the power supply unit can be prevented from being degraded by ozone even if a small amount of ozone is generated around the excimer lamp(s) in the housing. Furthermore, since the electrical connection between the power supply unit and the first and second electrodes can be established through the first and second electrical conductors extending through the housing, the structure of the ultraviolet irradiation device can be made highly versatile. Since the excimer lamp(s) is arranged in the housing, the excimer lamp(s) can be replaced by replacing the housing itself. Thus, the ultraviolet irradiation device has a highly convenient device structure.

The first and second electrodes may be in contact with the housing and fixed to the housing. A first connection between the first electrode and the first electrical conductor may be provided on a first surface of the housing that contacts the first electrode. A second connection between the second electrode and the second electrical conductor may be provided on a second surface of the housing that contacts the second electrode.

Thus, the electrical connections inside the housing do not utilize conductive members (wires). If wires are utilized for the electrical connections, the material covering the wires can be degraded by ozone and problems of short-circuiting and electricity leakage may occur. Since the ultraviolet irradiation device of the invention does not use wires for the electrical connections in the housing, the problems of the short-circuiting and electricity leakage can be avoided.

The first electrical conductor may have a first connection terminal that is electrically connected to the first electrode and extends through the housing, and a first conductive member connected to the first connection terminal and extend to the power supply unit. The second electrical conductor may have a second connection terminal that is electrically connected to the second electrode and extends through the housing, and a second conductive member connected to the second connection terminal and extend to the power supply unit. The first and second connection terminals may be electrically connected to the power supply unit via the first and second conductive members that extend outside the housing, respectively.

The first connection terminal is disposed on the contact surface between the housing and the first electrode and extends through a first through hole formed in the housing, and the second connection terminal is disposed on the contact surface between the housing and the second electrode and extends through a second through hole formed in the housing. Thus, areas around the first and second through holes are closed (sealed) by the first and second electrodes that contact the housing. Consequently, the electrical connections between the first and second electrodes and the power supply unit can be made more robust while maintaining the closed space inside the housing. It is also possible to prevent ultraviolet rays generated inside the housing from leaking through the through holes in which the first and second connection terminals extend because the areas around the through holes are sealed by the first and second electrodes that contact the housing. Furthermore, the use of the first and second connection terminals can facilitate the manufacturing process of the ultraviolet irradiation device, and can easily realize a power supply structure that connects to the first and second electrodes through the housing.

The first electrode and the second electrode may be in contact with the housing and fixed to the housing. The first connection terminal may extend from a first surface of the housing that contacts the first electrode, and the second connection terminal may extend from a second surface of the housing that contacts the second electrode.

If this configuration is employed, the electrical connections inside the housing do not use conductive members (wires). If wires are used for the electrical connections, the materials covering the wires are degraded by ozone, and short-circuiting and electricity leakage may occur. If wires are not used for the electrical connections in the housing, the short-circuiting and electricity leakage can be avoided. The first connection terminal is disposed on the contact surface between the housing and the first electrode and extends through a first through hole formed in the housing, and the second connection terminal is disposed on the contact surface between the housing and the second electrode and extends through a second through hole formed in the housing. Thus, areas around the first and second through holes are sealed by the first and second electrodes that contact the housing. Consequently, the electrical connections between the first and second electrodes and the power supply unit can be made more robust while maintaining the closed space inside the housing. It is also possible to prevent ultraviolet rays generated inside the housing from leaking through the through holes in which the first and second connection terminals extend because the areas around the through holes are sealed by the first and second electrodes that contact the housing.

The first and second connection terminals may be screw members that fix the first and second electrodes, respectively, to the housing. If the first and second connection terminals are screw members, the first and second connection terminals can also serve as mechanical connection members between the housing and the electrodes (members for fixing the electrodes to the housing).

The housing may have an upper frame part and a lower frame part such that the upper frame part and the lower frame part form, in combination, a closed space to receive the excimer lamp(s) therein. The light-emitting window may be formed in the upper frame part. The first and second electrodes may be fixed to the lower frame part, respectively. In this configuration is employed, the manufacturing and assembly of the ultraviolet irradiation device becomes easier.

The power supply unit may be disposed on an opposite side of the housing from a third surface of the housing in which the light-emitting window is formed. If this configuration is employed, the structure of the ultraviolet irradiation device becomes a most compact, easy to handle, and versatile structure.

The power supply unit may include an inverter and a cooling mechanism for cooling the inverter. If this configuration is employed, the power supply unit can be efficiently cooled.

The ultraviolet irradiation device may further include an optical filter over the light-emitting window such that the optical filter blocks transmission of UVC light whose wavelength is longer than 230 nm. If such optical filter is disposed over the light-emitting window, the ultraviolet irradiation device can emit light in the wavelength range that has less adverse effects on the human body.

The insulating and heat-resistant resin material may be any one of polytetrafluoroethylene (PTFE), ethylene-tetrafluoroethylene copolymer (ETFE), perfluoroalkoxyalkane (PFA), polyetherimide (PEI), glass fiber-containing polyphenylene sulfide (PPS-GF), liquid crystal polymers (LCP), and glass fiber-containing polybutylene terephthalate (PBT-GF). If such material is used for the housing, the housing is less degraded by ultraviolet rays and has sufficient heat resistance (100 degree C. or higher). If capability of blocking the UVC light and easiness of machining/processing are also considered in addition to the resistance to UV degradation and the heat resistance, polyetherimide (PEI) is the easiest to handle and most suitable.

The ultraviolet irradiation device according to one embodiment of the present invention includes one or more excimer lamps to emit light with the center wavelength in the range from 200 nm to 230 nm, and has a versatile device structure.

DETAILED DESCRIPTION OF EMBODIMENTS

Embodiments of the present disclosure will be described below with reference to the drawings.

Figure 1:
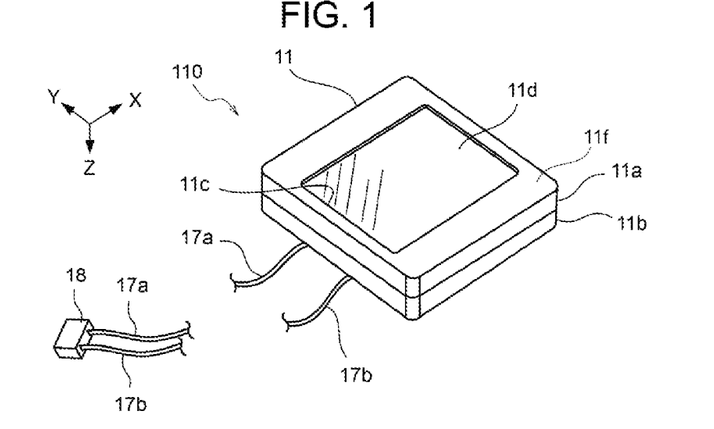
FIG. 1 shows a schematic perspective view of a light source unit of a ultraviolet irradiation device.
Figure 2A:
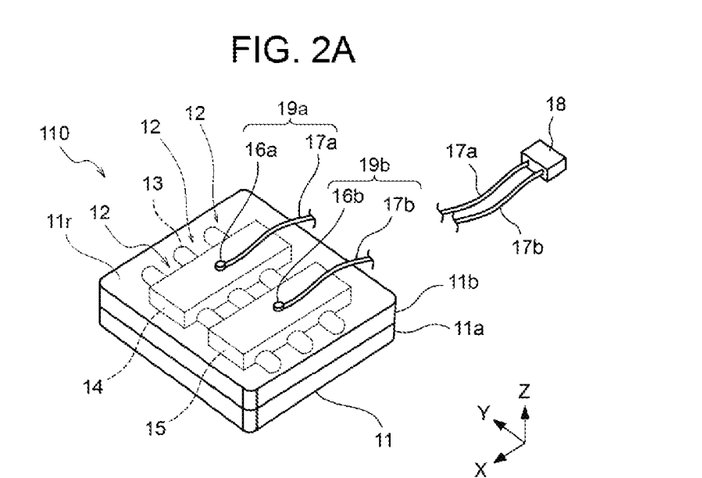
FIG. 2A is another schematic perspective view of the light source unit shown in FIG. 1 when viewed from an opposite direction and shows an internal structure of the light source unit.

FIG. 1 is an appearance view of a light source unit 110, which is the UV irradiation device in this embodiment. FIG. 1 is a front perspective view of the light source unit 110. FIG. 2A is a rear perspective view of the light source unit 110 and schematically shows the internal structure of the light source unit 110.

As shown in FIG. 1, the light source unit 110 includes a housing 11. The housing 11 has an upper frame (upper housing half) 11a and a lower frame (lower housing half) 11b. As shown in FIG. 2A, the light source unit 110 includes three excimer lamps 12 placed inside the housing 11. The three excimer lamps 12 extend in parallel to each other inside the housing 11. Each of the excimer lamps 12 emits light with a center wavelength in the range from 200 nm to 230 nm.

The housing 11 is made from an insulating and heat-resistant resin material. In this embodiment, the housing 11 is made from polyetherimide (PEI).

The material of the housing 11 can be any suitable resin material that is resistant to ultraviolet rays and has a sufficient heat resistance (100 degrees C. or higher), such as polytetrafluoroethylene (PTFE), ethylenetetrafluoroethylene copolymer (ETFE), perfluoroalkoxyalkane (PFA), polyetherimide (PEI), glass fiber-containing polyphenylene sulfide (PPS-GF), liquid crystal polymer (LCP), and glass fiber-containing polybutylene terephthalate (PBT-GF).

In order to verify in detail the degradation of the housing 11 caused by ultraviolet light of wavelengths of 200 nm to 230 nm, the inventors used a KrCl excimer lamp that emitted ultraviolet light with a peak wavelength of 222 nm and irradiated the housing 11 with the ultraviolet light at an illuminance of 15 mW/cm$^2$ for 20 minutes. The housings 11 made from polytetrafluoroethylene (PTFE), perfluoroalkoxyalkane (PFA), and polyetherimide (PEI) showed almost no UV degradation. Thus, the inventors confirmed that these materials are preferred as materials for the housing 11 of the light source unit 110.

Furthermore, if considered as a UV irradiation device that inactivates microorganisms and viruses without harming human cells, the housing of the light source (e.g., excimer lamps) is preferably made from a resin material that has a low transmittance of UVC light that harms human cells. For example, it is desirable for the resin material of the housing 11 to have almost no transmittance of UVC light with a wavelength longer than 230 nm (e.g., transmittance of 5% or less, more preferably 1% or less).

Therefore, the inventors verified the transmittance of UVC light using three types of sheet made from polytetrafluoroethylene (PTEF), perfluoroalkoxyalkane (PFA) and polyetherimide (PEI). The inventors confirmed that PTFE and PFA, which are highly resistant to UV degradation, have a transmittance of several percent to several tens of percent of UVC light if the PTFE sheet (or the PFA sheet) has a certain thickness (e.g., 1 mm). Accordingly, if this resin material is used for the housing of the excimer lamp, there is a possibility that harmful light may leak through the housing. When there is a concern in practical use, a light shielding element should be disposed around the housing.

Figure 3:
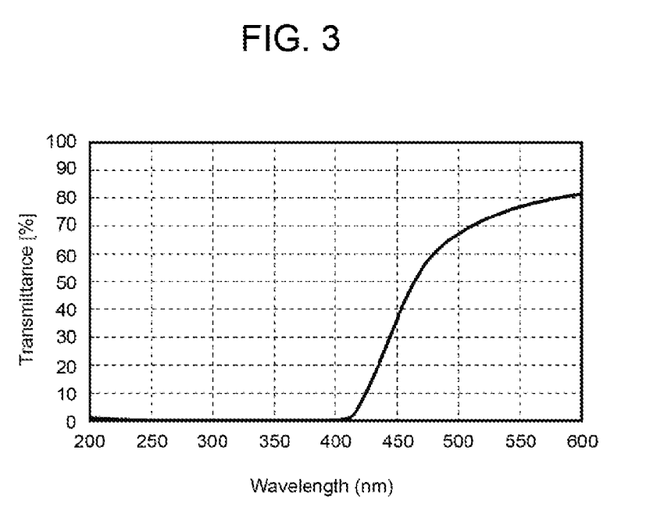
FIG. 3 shows the measured UV-VIS transmittance of a plate made from polyetherimide (PEI).

On the other hand, when PEI was used as the material for the housing, it was confirmed that the transmission of UVC light was suppressed quite effectively. FIG. 3 shows the results of measuring the UV-VIS (ultraviolet-visible) transmittance for the plate of polyetherimide material (PEI plate) with a thickness of 1 mm. As can be seen from FIG. 3, almost no light with a wavelength of 400 nm or less is transmitted through the PEI plate.

From the above-described considerations, it is most desirable to use polyetherimide (PEI) as the housing material.

The housing 11 has a structure that forms a closed space with no inflow of outside air and this structure is made by the upper frame part 11a and the lower frame part 11b. Thus, the housing 11 separates (isolates) the inside of the housing 11 from the outside of the housing 11. The excimer lamps 12 are housed in the closed space formed inside the housing 11 and covered by the housing 11.

The upper frame part 11a has an opening 11c that serves as a light-emitting window (light exit window). A window member 11d made of quartz glass, for example, is provided in the opening 11c. An optical filter or a similar element to block unnecessary light may also be provided at the opening 11c. For example, the optical filter may be disposed over the window member 11d in a front surface 11f of the housing 11. Each of the excimer lamps 12 is disposed in the housing 11 such that the light-emitting surface (front surface) of each of the excimer lamps 12 faces the window member 11d. Reference numeral 11r designates a rear surface of the housing 11.

It should be noted that although the light source unit 110 has the three excimer lamps 12 in FIG. 2A, the number of excimer lamps 12 is not limited to three.

Each of the excimer lamps 12 has a straight tube-shaped discharge vessel 13. The tube of the excimer lamp 12 has two opposite ends in its longitudinal direction (Y direction), and the two opposite ends are hermetically sealed. The discharge vessel 13 may be made of quartz glass, for example. A rare gas and halogen are enclosed and sealed, as the emitting gases, in the discharge vessel 13. In this embodiment, the rare gas is Kr and the halogen is Cl. Thus, a KrCl excimer lamp using krypton chloride (KrCl) gas is used as the excimer lamp 12. The KrCl excimer lamp 12 emits light whose center wavelength is 222 nm.

It should be noted that bromine (Br) may be used as the halogen. The KrBr excimer lamp emits light whose center wavelength is 207 nm.

A pair of electrodes (i.e., a first electrode 14 and a second electrode 15) are arranged in the housing 11 such that the first and second electrodes 14 and 15 are in contact with the outer surface of the discharge vessel 13 of each excimer lamp 12. The first electrode 14 extends in parallel to the second electrode 15. The first and second electrodes 14 and 15 extend in the X direction, i.e., the direction perpendicular to the longitudinal direction of the excimer lamps 12. As shown in FIG. 2A, the first and second electrodes 14 and 15 are placed on the rear surfaces of the discharge vessels 13, which are opposite to the light exit surface (i.e., the front surface), and spaced apart from each other in the tube axis direction (Y direction) of the discharge vessel 13. The rear surface of the discharge vessel 13 is a +Z direction surface.

Figure 2B:
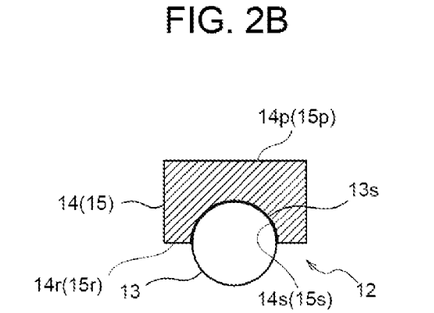
FIG. 2B shows a discharge vessel and an electrode of the light source unit shown in FIG. 2A when viewed in a longitudinal direction of the discharge vessel.

Each of the discharge vessels 13 spans the two electrodes 14 and 15 while contacting the two electrodes 14 and 15. As shown in FIG. 2B, each of the electrodes 14 and 15 has a concave groove 14s, 15s for each discharge vessel 13, and the discharge vessel 13 is fitted into the concave grooves 14s and 15s of the electrodes 14 and 15. The three grooves 14s are formed in a surface 14r of the first electrode 14 and the three grooves 15s are formed in a surface 15r of the second electrode 15 such that the three excimer lamps 12 are partially fitted in the three pairs of grooves 14s and 15s, respectively.

Of the two electrodes 14 and 15, one electrode (e.g., the first electrode 14) is the high-voltage electrode, and the other electrode (e.g., the second electrode 15) is the low-voltage electrode (ground electrode). By applying a high-frequency voltage between the first and second electrodes 14 and 15, excited complex (exciplex) is generated in the inner space of the discharge vessel 13, and excimer light with a center wavelength of 222 nm is emitted from the light-emitting surface of the excimer lamp 12.

In this embodiment, the surface 14p, 15p of the electrode 14, 15, which is the surface opposite to the surface 14r, 15r having the concave groove 14s, 15s, is fixed onto the surface of the lower frame part 11b (onto the surface facing the light-emitting window 11d of the upper frame part 11a). Thus, the light-emitting surface of each of the excimer lamps 12 faces the light-emitting window 11d. Therefore, the light emitted from each of the excimer lamps 12 exits from the light source unit 110 through the light-emitting window 11d.

The electrodes 14 and 15 may be made from metal members that are reflective to the light emitted from the excimer lamps 12. If the electrodes 14 and 15 reflect the light emitted from the excimer lamps 12, the light radiated in the +Z direction from the discharge vessels 13 of the excimer lamps 12 are reflected by the electrodes 14 and 15 such that the reflected light travels in the −Z direction.

As mentioned earlier, the optical filter may be provided at the opening 11c, which may extend over the light exit window 11d. The optical filter can be, for example, a wavelength-selecting filter that transmits light in the wavelength range from 190 nm to 237 nm (more preferably, light in the wavelength range from 190 nm to 230 nm), which has less adverse effects on the human body, and blocks light in other wavelength ranges to block UVC light. For example, the optical filter may have dielectric multilayers that are constituted by $HfO_2$ and $SiO_2$ layers.

Alternatively, the optical filter (wavelength-selecting filter) may have dielectric multilayers that are constituted by $SiO_2$ and $Al_2O_3$ layers.

When the optical filter has the dielectric multilayers made of $HfO_2$ and $SiO_2$ layers, the total number of layers can be reduced compared to the optical filter that has the dielectric multilayers made of $SiO_2$ and $Al_2O_3$ layers. Therefore, if the optical filter has the dielectric multilayers made of $HfO_2$ and $SiO_2$ layers, the transmittance of ultraviolet rays at an incident angle of zero degree can be increased.

Thus, even if a small amount of light harmful to humans is emitted from the excimer lamps 12, the optical filter disposed over the light exit window 11d can suppress the leakage of the harmful light from the housing 11 more reliably. It should be noted that the location of the optical filter may be arbitrary as long as the harmful light is blocked by the optical filter and does not travel to the outside from the housing 11.

The first electrode 14 and the second electrode 15 are electrically connected to a power supply unit 120 (FIG. 4) that supplies electricity to the excimer lamps 12. In this embodiment, the power supply unit is located outside the housing 11. The power supply unit 120 will be described in detail with reference to FIG. 4.

As shown in FIG. 2A, the light source unit 110 has a first connection terminal 16a, which extends from the first electrode 14 and reaches the outer surface of the housing 11, and a first conductive member (first wire) 17a, which electrically connects the first connection terminal 16a to the power supply unit. The first connection terminal 16a is a metal member electrically connected to the first electrode 14 and extends through the housing 11. A combination of the first connection terminal 16a and the first conductive member 17a electrically connects the first electrode 14 to the power supply unit, and is referred to as a first connection member (first electrical conductor) 19a.

The first connection terminal 16a is provided on the contact surface between the housing 11 and the first electrode 14, and can be a screw member that penetrates the contact surface and fixes the first electrode 14 to the housing 11. In other words, the screw head of the first connection terminal 16a is situated outside the housing 11 and on that surface of the housing 11 which contacts the first electrode 14. One end of the first conductive member 17a is connected to the screw head of the first connection terminal 16a outside the housing 11, and the other end is connected to the power supply unit. In this way, the first conductive member 17a electrically connects the first connection terminal 16a to the power supply unit outside the housing 11, and the electrical connection inside the housing 11 does not use wires.

Similarly, the light source unit 110 has a second connection terminal 16b, which is electrically connected to the second electrode 15 and extends through the housing 11, and a second conductive member (electric wire) 17b, which electrically connects the second connection terminal 16b to the power supply unit. A combination of the second connection terminal 16b and the second conductive member 17b is a second connection member (second electric conductor) 19b that electrically connects the second electrode 15 to the power supply unit. The configuration of the second connection member 19b is the same as the configuration of the first connection member 19a.

The first conductive member 17a and the second conductive member 17b extend to a single (or common) connector 18 that can be connected to and disconnected from the power supply unit. The electrical connection between the first and second connection terminals 16a and 16b and the power supply unit can be easily established by the connector 18.

Because the light source unit 110 has the above-described configuration, the light source unit 110 can be easily attached to and detached from the power supply unit by attaching and detaching the connector 18. Therefore, when the excimer lamps 12 placed in the housing 11 need to be replaced, the housing 11 itself may be replaced (the excimer lamps are present in the housing 11). Thus, the light source unit 110 has a highly convenient device structure.

Figure 4:
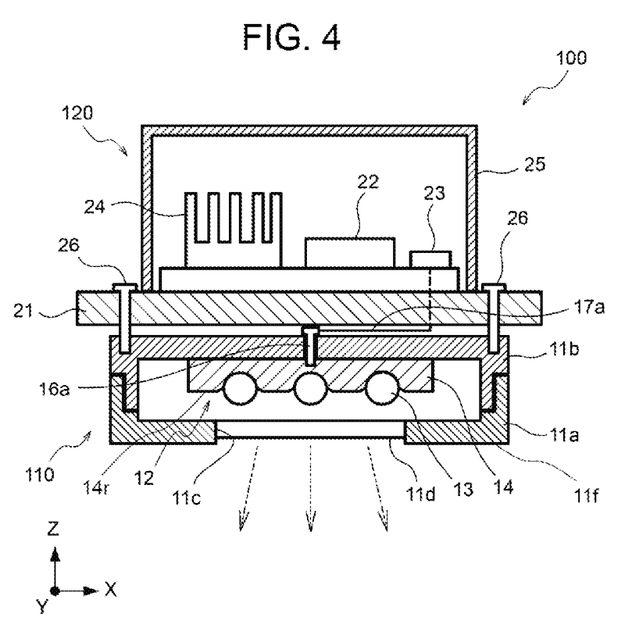
FIG. 4 shows a schematic cross-sectional view of the ultraviolet irradiation device.

FIG. 4 is a schematic diagram of a UV irradiation device 100 equipped with the power supply unit 120.

As shown in FIG. 4, the ultraviolet irradiation device 100 includes the light source unit 110 and the power supply unit 120.

The power supply unit 120 has a support element 21, a power supply component 22, a connect section 23, and a cooling member (cooling mechanism) 24. The power supply component 22, the connect section 23, and the cooling member 24 are disposed on the support element 21, and are covered by a shielding element 25. The light source unit 110 is located below the support element 21 and emits light downward as indicated by the broken-line arrows.

The power supply component 22 includes a power supply and an inverter to which power from the power supply is supplied. The first conductive member 17a and the second conductive member 17b (not shown in FIG. 4) are connected to the connect section 23. The cooling member 24 is a member for cooling the power supply component 22 and can be, for example, a heat sink. The cooling member 24 is not limited to the heat sink, but may be, for example, a cooling fan.

The power supply unit 120 is placed on the back face of the housing 11 of the light source unit 110 (opposite to the light exit window 11d) as the support element 21 is fixed to the lower frame part llb of the housing 11 by the fixing elements 26.

As described above, the ultraviolet irradiation device 100 of this embodiment includes the light source unit 110 that has the housing 11 and the excimer lamps 12 arranged in the housing 11. The housing 11 is made from an insulating and heat-resistant resin material. The housing 11 receives the excimer lamps 12 therein and has the light exit window 11d that allows light with a center wavelength of 200 nm to 230 nm emitted from the excimer lamps 12 to proceed out of the housing 11. The emitted light is indicated by the downward arrows in FIG. 4. The power supply unit 120, which supplies power to the excimer lamps 12, is located outside the housing 11. The first electrode 14 of the excimer lamps 12 and the power supply unit 120 are electrically connected by the first connection member (first conductor) 19a that penetrates the housing 11, and the second electrode 15 of the excimer lamps 12 and the power supply unit 120 are electrically connected by the second connection member (second conductor) 19b that penetrates the housing 11.

Specifically, the first connection member 19a has the first connection terminal 16a electrically connected to the first electrode 14 and extending through the housing 11, and the first conductive member 17a electrically connecting the first connection terminal 16a to the power supply unit 120 outside the housing 11. Similarly, the second connection member 19b has the second connection terminal 16b electrically connected to the second electrode 15 and extending through the housing 11, and the second conductive member 17b electrically connecting the second connection terminal 16b to the power supply unit 120 outside the housing 11.

As described above, the housing 11 made from the heat-resistant resin material is configured to cover (surround, enclose) the excimer lamps 12, and the inside of the housing 11 is separated from the outside of the housing 11. The power supply unit 120 is located outside the housing 11.

If the light emitted from the excimer lamps 12 contains even a small amount of ultraviolet rays with a wavelength of less than 190 nm, the ultraviolet rays will act on the oxygen around the excimer lamps to produce ozone. By enclosing the excimer lamps 12 in the housing 11 made from the heat-resistant resin material and placing the power supply unit 120 outside the housing 11, the electronic components that make up the power supply unit 120 can be prevented from being degraded by the ozone even if ozone is generated around the excimer lamps 12 in the housing 11.

The excimer lamps 12 are enclosed by the housing 11, and the closed space is formed inside the housing 11 with no inflow of the outside air. Therefore, while the excimer lamps 12 are lit, the temperature inside the housing 11 rises due to the heat emitted from the excimer lamps 12. Since the housing 11 is made from the heat-resistant resin material, the heat inside the housing 11 is not easily dissipated. Consequently, the housing 11 can keep the excimer lamps 12 warm (or hot).

The half-life of ozone shortens as the temperature increases. Therefore, the heat retention inside the housing 11 has the effect of facilitating the thermal decomposition of the ozone generated inside the housing 11.

The quartz glass, which constitutes the discharge vessel 13, may accumulate distortion due to the long hours of UV irradiation. Such distortion in the quartz glass can be expected to be alleviated by heat. In other words, by making it difficult for the heat inside the housing 11 to be dissipated and making it easy for the excimer lamps 12 to retain its heat, the housing 11 can alleviate the distortion of the quartz glass, which makes up the discharge vessel 13, caused by the ultraviolet light.

On the other hand, the power supply unit 120 has the inverter or the like for applying high-frequency high voltage to the excimer lamps 12. The power supply unit 120 tends to generate heat when the power supply unit 120 continues the lighting operation of the excimer lamps 12. Therefore, the cooling mechanism (cooling member) 24 is provided to cool the power supply unit 120.

If the excimer lamps 12 and the power supply unit 120 are placed in the same space (including spaces that communicate with each other), the excimer lamps 12 are cooled by the cooling mechanism 24 which is provided for the purpose of cooling the power supply unit 120. When the excimer lamps 12 are overcooled, the quartz glass that constitutes the discharge vessels 13 is likely to be distorted by the ultraviolet light emitted from the excimer lamps 12.

In contrast, in this embodiment, since the power supply unit 120 is placed outside the housing 11, only the power supply unit 120 can be properly cooled by the cooling mechanism 24. Thus, the lighting of the light source unit 110 can properly continue without overcooling the excimer lamps 12.

Because the ultraviolet irradiation device 100 of this embodiment can establish the electrical connection with the power supply unit 120 through the connection terminals 16a and 16b provided through the housing 11, a compact and highly versatile device structure can be realized. Manufacturing the ultraviolet irradiation device 100 is easy, and a power supply structure that is connected to the electrodes 14 and 15 through the housing 11 can be easily realized.

Because the connection terminals 16a and 16b are disposed on the contact surface between the housing 11 and the electrodes 14 and 15, no conductive members (wires) extend in the housing 11 to make the electrical connection. Therefore, ozone-induced deterioration of the material covering the wires in the housing 11 would not occur, and the problems of short-circuiting and electricity leakage can be avoided. The electrical connection between the electrodes 14, 15 and the power supply unit 120 can be made more robust while maintaining the closed space in the housing 11.

Because the connection terminals 16a and 16b are the screws that fix the electrodes 14 and 15 to the housing 11, respectively, the connection terminals 16a and 16b can also serve as mechanical connections (fixing of electrodes) between the housing 11 and the electrodes 14 and 15.

Because the power supply unit 120 is placed on the opposite side of the housing 11 from the front surface 11f of the housing 11 where the light exit window 11d is formed, the ultraviolet irradiation device 100 can have a most compact structure. This structure is also easy to handle and versatile.

Because the connection terminals 16a and 16b are disposed on the surface of the housing 11 where the electrodes 14 and 15 contact, the connection terminals 16a and 16b can be placed closest to the power supply unit 120. Thus, routing of the conductive members 17a and 17b is easy.

The excimer lamps 12 have the first electrode 14 and the second electrode 15 that are spaced from each other in the first direction (Y direction) and have the grooves 14s and 15s formed on the front surfaces 14r and 15r thereof. The grooves 14s and 15s extend in the first direction. Each of the excimer lamps 12 has the discharge vessel 13 that is partly fitted into the associated grooves 14s and 15s of the first electrode 14 and the second electrode 15 and extends across the first electrode 14 and the second electrode 15. The discharge vessel 13 extends in the first direction to span the first electrode 14 and the second electrode 15. This configuration enables the discharge vessel 13 of each excimer lamp 12 to perform the discharging although the discharge vessel 13 is simply a straight tube. This allows for a much smaller device size than, for example, an excimer lamp equipped with a discharge vessel of a double-tube structure.

As described above, the ultraviolet irradiation device 100 of this embodiment includes the excimer lamps 12 that emit light with the center wavelength in the range from 200 nm to 230 nm, and can be a compact ultraviolet irradiation device having a versatile device structure. The ultraviolet irradiation device 100 can use the original (or inherent) capabilities of the ultraviolet light for sterilization and virus inactivation without causing erythema and keratitis in human's eyes and skins and animal's skin and eyes. In particular, unlike conventional devices for emitting ultraviolet light, the ultraviolet irradiation device 100 of the embodiment can be used in an environment in which people exist. The ultraviolet irradiation device 100 may be placed anywhere in an environment in which people exist, regardless of indoor or outdoor, and can emit the ultraviolet light in the wavelength range from 200 nm to 230 nm over the entire space of the environment. Thus, the device 100 can reduce and sterilize bacteria and/or viruses in the air and on surfaces of all objects in the environment. This matches Goal 3 of the SDGs advocated by United Nations "Ensure healthy lives and promote well-being for all at all ages" and greatly contributes to Target 3.3 "By 2030, end the epidemics of AIDS, tuberculosis, malaria and neglected tropical diseases and combat hepatitis, water-borne diseases and other communicable diseases."

In the above-described embodiment, the power supply structure from the power supply unit 120 to the electrodes 14 and 15 includes a combination of the connection terminals 16a and 16b and the conductive members 17a and 17b. It should be noted, however, that the power supply structure from the power supply unit 120 to the electrodes 14 and 15 is not limited to the above-described structure. For example, the electrodes 14, 15 and the power supply unit 120 may be directly connected by conductive members (wires) extending through the housing 11. In other words, the first connection member (first conductor) 19a and the second connection member (second conductor) 19b may be composed solely of conductive members.

While certain embodiments and modifications have been described, these embodiments and modifications have been presented by way of examples only, and are not intended to limit the scope of the present invention. The novel apparatuses and methods thereof described herein may be embodied in a variety of other forms; furthermore, various omissions, substitutions and changes in the form of the apparatuses and methods thereof described herein may be made without departing from the gist of the present invention. The appended claims and their equivalents are intended to cover such forms or modifications as would fall within the scope and gist of the present invention.

The present application is based upon and claims the benefit of a priority from Japanese Patent Application No. 2020-146836, filed Sep. 1, 2020, and the entire content of which is incorporated herein by reference.

What is claimed is:

1. A device for emitting ultraviolet light, the device comprising:
   at least one excimer lamp, each of the at least one excimer lamp having a discharge vessel filled with light-emitting gases, and a pair of first and second electrodes that are placed in contact with the discharge vessel and produce a dielectric barrier discharge inside the discharge vessel, and
   a housing made from an insulating and heat-resistant resin material, the housing configured to house the at least one excimer lamp, and having a light-emitting window that allows light with a center wavelength in a range from 200 nm to 230 nm emitted from the at least one excimer lamp to exit from the housing,
   wherein the housing forms a closed space for housing the at least one excimer lamp.

2. The device for emitting ultraviolet light according to claim 1 further including:
   a first electrical conductor electrically connected to the first electrode and extending through the housing, and
   a second electrical conductor electrically connected to the second electrode and extending through the housing, and
   wherein the first and second electrical conductors are electrically connected to a power supply unit that supplies power to the at least one excimer lamp, and the power supply unit is disposed outside the housing.

3. The device for emitting ultraviolet light according to claim 2, wherein the first and second electrodes are in contact with the housing and fixed to the housing,
   a first connection between the first electrode and the first electrical conductor is provided on a first surface of the housing that contacts the first electrode, and
   a second connection between the second electrode and the second electrical conductor is provided on a second surface of the housing that contacts the second electrode.

4. The device for emitting ultraviolet light according to claim 2, wherein the first electrical conductor has a first connection terminal that is electrically connected to the first electrode and extends through the housing, and a first conductive member connected to the first connection terminal,
   the second electrical conductor has a second connection terminal that is electrically connected to the second electrode and extends through the housing, and a second conductive member connected to the second connection terminal, and the first and second connection terminals are electrically connected to the power supply unit via the first and second conductive members outside the housing, respectively.

5. The device for emitting ultraviolet light according to claim 4, wherein the first electrode and the second electrode are in contact with the housing and fixed to the housing,
the first connection terminal is provided on a first surface of the housing that contacts the first electrode, and
the second connection terminal is provided on a second surface of the housing that contacts the second electrode.

6. The device for emitting ultraviolet light according to claim 4, wherein the first and second connection terminals are screw members that fix the first and second electrodes, respectively, to the housing.

7. The device for emitting ultraviolet light according to claim 2, wherein the housing has an upper frame part and a lower frame part such that the upper frame part and the lower frame part form a closed space to receive the at least one excimer lamp therein,
the light-emitting window is formed in the upper frame part, and
the first and second electrodes are fixed to the lower frame part, respectively.

8. The device for emitting ultraviolet light according to claim 2, wherein the power supply unit is disposed on an opposite side of the housing from a third surface of the housing in which the light-emitting window is disposed.

9. The device for emitting ultraviolet light according to claim 2, wherein the power supply unit includes an inverter and a cooling mechanism for cooling the inverter.

10. The device for emitting ultraviolet light according to claim 1 further including an optical filter over the light-emitting window such that the optical filter blocks transmission of UVC light whose wavelength is longer than 230 nm.

11. The device for emitting ultraviolet light according to claim 1, wherein the insulating and heat-resistant resin material is any one of polytetrafluoroethylene (PTFE), ethylene-tetrafluoroethylene copolymer (ETFE), perfluoroalkoxyalkane (PFA), polyetherimide (PEI), glass fiber-containing polyphenylene sulfide (PPS-GF), liquid crystal polymers (LCP), and glass fiber-containing polybutylene terephthalate (PBT-GF).

12. The device for emitting ultraviolet light according to claim 1, wherein the insulating and heat-resistant resin material is polyetherimide (PEI).

* * * * *